(12) United States Patent
Hayakawa et al.

(10) Patent No.: US 10,442,669 B2
(45) Date of Patent: Oct. 15, 2019

(54) DRINK FILLING METHOD

(71) Applicant: DAI NIPPON PRINTING CO., LTD., Tokyo (JP)

(72) Inventors: Atsushi Hayakawa, Tokyo (JP); Yuiko Wada, Tokyo (JP)

(73) Assignee: Dai Nippon Printing Co., Ltd., Shinjuku-Ku (JP)

( * ) Notice: Subject to any disclaimer, the term of this patent is extended or adjusted under 35 U.S.C. 154(b) by 346 days.

(21) Appl. No.: 14/650,737

(22) PCT Filed: Dec. 17, 2013

(86) PCT No.: PCT/JP2013/083692
§ 371 (c)(1),
(2) Date: Jun. 9, 2015

(87) PCT Pub. No.: WO2014/098058
PCT Pub. Date: Jun. 26, 2014

(65) Prior Publication Data
US 2016/0185584 A1 Jun. 30, 2016

(30) Foreign Application Priority Data

Dec. 21, 2012 (JP) ................... 2012-280093

(51) Int. Cl.
*B67C 7/00* (2006.01)
*B08B 9/027* (2006.01)
(Continued)

(52) U.S. Cl.
CPC ............ *B67C 7/0073* (2013.01); *B08B 9/027* (2013.01); *B67C 3/001* (2013.01); *A61L 2/18* (2013.01)

(58) Field of Classification Search
CPC .. B67C 7/0073; B67C 3/001; A61L 2/18–186
See application file for complete search history.

(56) References Cited

U.S. PATENT DOCUMENTS 3,693,640 A 9/1972 Wettlen et al.
4,878,951 A * 11/1989 Pochard .................. A23C 7/02
134/22.17
(Continued)

FOREIGN PATENT DOCUMENTS

JP 50-38995 12/1975
JP 06-220496 A 8/1994
(Continued)

OTHER PUBLICATIONS

Extended European Search Report dated Dec. 19, 2016: Appln. No. 16184788.4-1703.
(Continued)

*Primary Examiner* — Timothy C Cleveland
(74) *Attorney, Agent, or Firm* — Burr & Brown, PLLC (57) ABSTRACT

It is possible to shorten a time before starting a drink filling working and a time for manufacturing a product. In a drink filling method in which a drink supply pipe line (7) for supplying a sterilized drink from a heat-sterilizing unit (18) into a filling machine (2) is sterilized, the drink then fills a container (4) through the drink supply pipe line (7), and thereafter, the container (4) is sealed, an upstream side circulation path (6a) is formed by forming an upstream side return path to an upstream side pipe line section (7a) passing through the sterilizing unit of the drink supply pipe line, a downstream side circulation path (6b) is formed by forming a downstream side return path to an downstream side pipe line section (7b) of the drink supply pipe line extending from a downstream side portion of the upstream side pipe line section to the filling machine, an alkaline cleaning liquid is circulated within the upstream side circulation path and the downstream side circulation path to thereby clean and sterilize an interior of the drink supplying pipe line, and a (Continued)

drink filling working is stared after performing a rinsing treatment with water.

7 Claims, 7 Drawing Sheets

(51) Int. Cl.
  *B67C 3/00* (2006.01)
  *A61L 2/18* (2006.01)

(56) References Cited

U.S. PATENT DOCUMENTS

| | | | |
|---|---|---|---|
| 2008/0142041 A1* | 6/2008 | Fischer | B01D 65/02 134/10 |
| 2012/0000492 A1 | 1/2012 | Katzenbacher et al. | |

FOREIGN PATENT DOCUMENTS

| | | |
|---|---|---|
| JP | 06-264097 A | 9/1994 |
| JP | 2000-153245 A | 6/2000 |
| JP | 2002-205067 A | 7/2002 |
| JP | 2004-066159 A | 3/2004 |
| JP | 2007-002014 A | 1/2007 |
| JP | 2007-022600 A | 2/2007 |
| JP | 2007-236706 A | 9/2007 |
| JP | 2007-331801 A | 12/2007 |
| JP | 2011-255938 A | 12/2011 |
| WO | 2006032731 A1 | 3/2006 |

OTHER PUBLICATIONS

Extended European Search Report dated Oct. 5, 2016: PCT/JP2013083692.

International Search Report dated Apr. 1, 2014; PCT/JP2013/083692.

* cited by examiner

DRINK FILLING METHOD

TECHNICAL FIELD

The present invention relates to a method of filling a container, such as PET bottle, with a drink after preliminarily cleaning and sterilizing a drink supply pipe line.

BACKGROUND TECHNOLOGY

In a conventional technology, an interior of a drink supply pipe line of an aseptic drink filling system is subjected to a CIP (Cleaning In Place) treatment and an SIP (Sterilizing In Place) treatment periodically or at a time when a kind of drink is changed (for example, refer to Patent Documents 1, 2 and 3).

The CIP treatment is performed, for example, by flowing a cleaning liquid prepared with water to which alkaline chemical agent such as caustic soda is added in a flow path from an inside of a pipe line of a drink filling path to a filling nozzle of a filling machine, and thereafter, by flowing a cleaning liquid prepared with water to which acidic chemical agent is added. According to such treatment, remaining content of preliminarily filled drink adhering to the drink filling path can be removed (for example, refer to Patent Documents 1, 2 and 3).

The SIP treatment is performed, for example, by circulating steam or hot water through the drink filling path cleaned by the CIP treatment mentioned above. According to such treatment, the interior of the drink filling path can be sterilized by the steam, hot water or like to thereby provide an aseptic condition in the drink filling path (see, for example, paragraph [0003] of Patent Document 3).

PRIOR ART DOCUMENT

Patent Document

Patent Document 1: Japanese Patent Laid-open Publication No. 2007-331801
Patent Document 2: Japanese Patent Laid-open Publication No. 2000-153245
Patent Document 3: Japanese Patent Laid-open Publication No. 2007-22600

SUMMARY OF THE INVENTION

Problem to be Solved by the Invention

In the conventional technology, when it is required to perform the CIP treatment to the inside of the drink supply pipe line by using alkaline cleaning liquid, the cleaning liquid is first dissolved with gas to thereby utilize foaming function thereof during the cleaning (for example, refer to Patent Document 1), and thereafter, the drink supply pipe line is rinsed with carbonic water after cleaning with the cleaning liquid (for example, refer to Patent Document 2), thereby enhancing the cleaning effect. Then, after the CIP treatment, hot water, steam, water containing a sterilizing agent or like is supplied so as to flow inside the drink supply pipe line, thus performing the SIP treatment.

Further, there is also provided a technology in which such SIP treatment is eliminated by performing the CIP treatment by supplying a filtrated cleaning liquid mixed with aseptic water into the drink supply pipe line.

However, the former method, mentioned above, in which the CIP treatment is performed with the cleaning liquid and then the SIP treatment is performed with hot water or like, requires much time and labour before starting a drink filling working. On the other hand, the latter method, mentioned above, in which the SIP treatment can be eliminated by performing the CIP treatment through filtration of the cleaning liquid, but such a filter for sterilization having resistant property against alkaline cleaning liquid is expensive in cost, and in addition, it is difficult to maintain and manage aseptic characteristics.

An object of the present invention is to provide a drink filling method capable of solving the problems mentioned above.

Means for Solving the Problem

With concentrated mind of the inventor of the subject application to solve the above problems, the inventor found out that an SIP treatment can be performed at the same time, by using a non-sterilized alkaline cleaning liquid, under predetermined conditions for a CIP treatment.

The present invention was conceived in accordance with the above finding and is characterized by being provided with the following configuration or structure.

It is further to be noted that although, in the following, reference numerals described in the drawings are added with parentheses for easy understanding of the present invention, the present invention is not limited to them.

That is, the invention according to claim 1 adopts a drink filling method in which cleaning and sterilizing treatments of a drink supply pipe line used this time for supplying a drink are performed at the same time by flowing alkaline cleaning liquid for delivering the drink from a drink sterilizing unit (18) into a filling machine (2), and rinsing treatment of an interior of the drink supply pipe line (7) is then performed with a water treated with sterilizing effect more than that allowable for a drink to be subsequently supplied, and thereafter, subsequent drink supply is started.

The invention according to claim 1 adopts a drink filling method in which a drink supply pipe line (7) for supplying a drink from a sterilizing unit (18) into a filling machine (2) is sterilized, the drink then fills a container (4) that has been sterilized with the drink supplied from the drink supply pipe line (7), and thereafter, the container (4) is sealed, wherein an upstream side circulation path is formed by forming an upstream side return path (6*a*) to an upstream side pipe line section (7*a*) passing through the sterilizing unit (18) of the drink supply pipe line (7), a downstream side circulation path is formed by forming a downstream side return path (6*b*) to an downstream side pipe line section (7*b*) of the drink supply pipe line extending from a downstream side portion of the upstream side pipe line section (7*a*) to the filling machine (2), an alkaline cleaning liquid is circulated within the upstream side circulation path and the downstream side circulation path to thereby clean and sterilize an interior of the drink supplying pipe line (7), and a drink filling process is stared after performing a rinsing treatment with water.

As recited in claim 3, in the drink filling method according to claim 1 or 1, it may be preferred that the water used for the rinsing treatment is set to have the same temperature as that of the drink to be filled.

As recited in claim 4, in the drink filling method according to any one of claims 1 to 3, it may be desired that the alkaline cleaning liquid is a cleaning liquid including at least 0.1-10 mass % of sodium hydroxide or potassium hydroxide.

As recited in claim 5, in the drink filling method according to any one of claims 1 to 4, it may be desired that the alkaline cleaning liquid is a cleaning liquid at least including sodium hypochlorite having chloride concentration of 100-3,000 ppm.

As recited in claim 6, in the drink filling method according to any one of claims 1 to 5, it may be desired that the alkaline cleaning liquid is supplied by being heated to a temperature of 50-150° C.

As recited in claim 7, in the drink filling method according to any one of claims 1 to 6, it may be desired that the alkaline cleaning liquid is circulated for 5-120 minutes.

As recited in claim 8, in the drink filling method according to any one of claims 1 to 7, it may be desired that the alkaline cleaning liquid is supplied with addition of a bleaching agent.

Effect of the Invention

According to the present invention, since the SIP treatment can be achieved simultaneously as well as the performance of the CIP treatment, the cleaning and sterilization of an aseptic drink filling system can be easily and speedily performed, and accordingly, production time for changing a certain kind of drink with another kind of drink can be shortened, thereby improving the production efficiency.

EMBODIMENT FOR CARRYING OUT THE INVENTION

Exemplary Embodiment 1

Hereunder, an exemplary embodiment 1 of the present invention will be explained with reference to the drawings.

First, a structure or configuration of an aseptic drink filling system is explained, and then, a cleaning method and a sterilizing method for this aseptic drink filling system will be explained.

Figure 1:
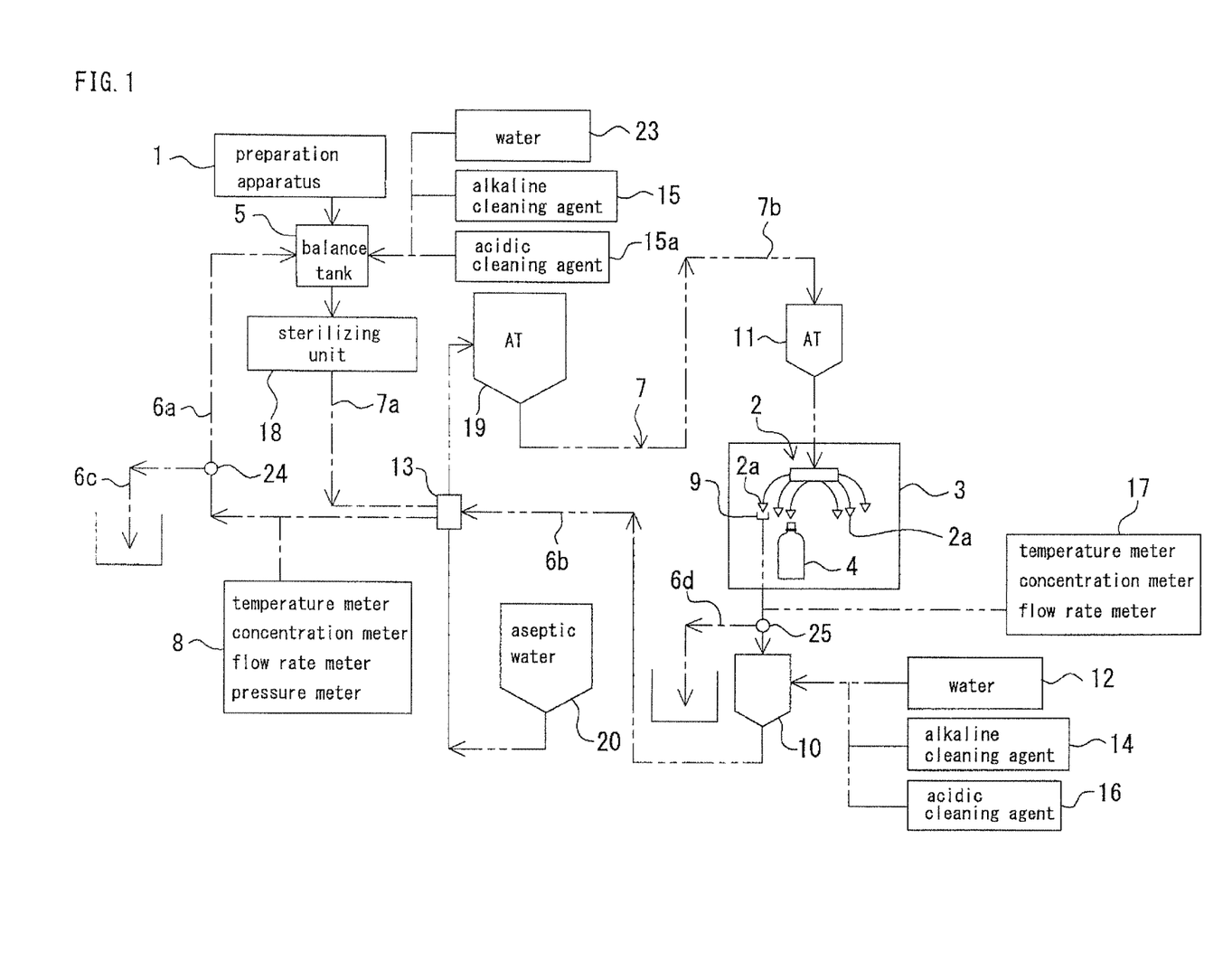
FIG. 1 is a block diagram of an aseptic drink filling system for carrying out a drink filling method according to one embodiment of the present invention.

As shown in FIG. 1, the aseptic drink filling system is provided with a drink preparation apparatus 1 and a filling machine 2 filling a bottle 4 with a drink. The drink preparation apparatus 1 and a filling nozzle: 2a of the filling machine 2 are connected through a drink supply pipe line 7. Further, the filling machine 2 is surrounded by an aseptic chamber 3.

The preparation apparatus 1 is an apparatus for preparing, for example, tea drink, fruit drink and the like at a predetermined composition rate (blended rate), and since such preparation apparatus 1 is known one, detailed explanation thereof is omitted herein.

The filling machine 2 is a machine provided with a wheel (not shown) that rotates a number of filling nozzles 2a at high speed in a horizontal plane, and this machine is for filling bottles 4 travelling in synchronism with a peripheral speed of the wheel disposed under the filling nozzles 2a with a constant amount of drink from the filling nozzles 2a, respectively, while rotating in conformity with the rotation of the wheel. Further, as such filling machine 2, a rotary type or linear type may be utilized, and since this filling machine 2 is also known one, detailed explanation thereof is accordingly omitted herein.

Further, a container which is filled up with a drink is a bottle made of, for example, polyethylene terephthalate (PET) or polyethylene (PE).

The drink supply pipe line 7 of the drink filling system is provided with a balance tank 5, a heat sterilizing unit (UHT (Ultra High-Temperature) unit or section) 18, a manifold valve 13, an aseptic surge tank 19, and a head tank 11 in this order from the upstream side toward the downstream side in view of the drink flow direction in the pipe line from the preparation apparatus 1 toward the filling machine 2.

Further, since the balance tank 5, the UHT 18, the manifold valve 13, the aseptic surge tank 19, and the head tank 11 are all known ones, so that detailed explanations thereof are omitted herein.

Figure 2:
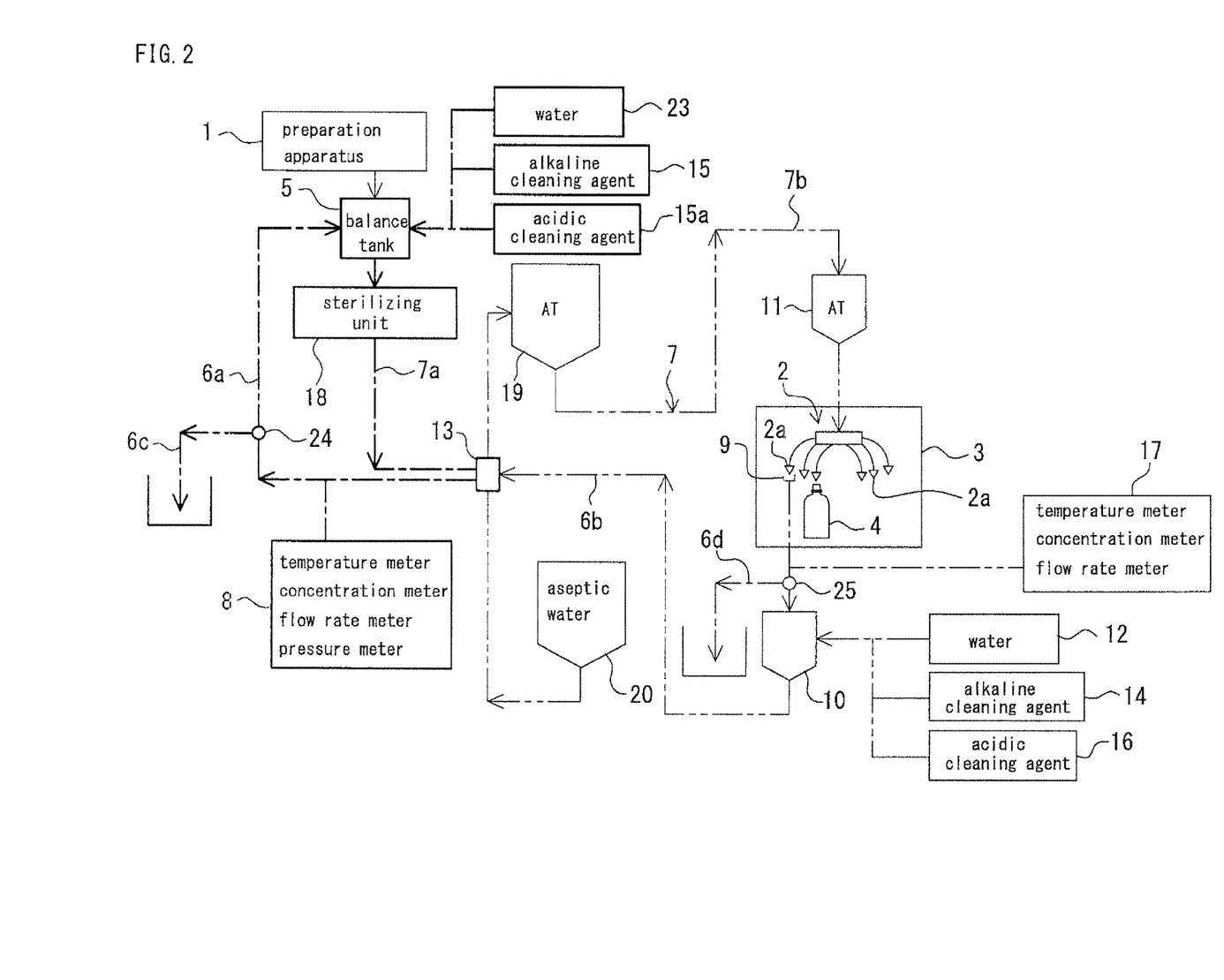
FIG. 2 is a block diagram of the aseptic drink filling system showing a state in which a CIP treatment is performed to an upstream side pipe line section of the drink filling system.

As shown in FIG. 2 with a thick line, an upstream side pipe line section 7a of the drink supplying pipe line 7 extending to the manifold valve 8 through the balance tank 5 and the UHT unit 18 is provided with an upstream side return path 6a to thereby constitute an upstream side circulation path for carrying out the cleaning and sterilizing treatments. A drain pipe 6c is branched from the upstream side return path 6a through a valve 24.

A water supply source 23 and an alkaline cleaning liquid supply source 15 are connected to the balance tank 5 through supply pipes, respectively. Various measurement equipments 8 are provided for the upstream side return path 6a for detecting temperature, concentration, flow rate, pressure and the like of the alkaline cleaning liquid flowing in the upstream side circulation path supplied from the alkaline cleaning liquid supply source 15.

Further, as occasion demands, an acidic cleaning liquid supply source 15a may be connected to the balance tank 5.

Further more, the alkaline cleaning liquid supplied from the alkaline cleaning liquid supply source 15 may include, as alkaline component, desired one of sodium hydrate, potassium hydrate, chlorinated alkaline such as sodium hypochlorite, or the like.

Still furthermore, the alkaline cleaning liquid may include: organic acid such as citric acid, succinic acid, or gluconic acid, or phosphoric acid and their alkaline metallic salt, alkaline earth metallic salt, and ammonium salt; metal ion sequestering agent such as hydroxyl carbonic acid compound such as alkanolamine salt such as ethylenediamine tetraacetate or like; anion surfactant, cationic surfactant, non-ionic series surfactant such as polyoxyethylene-alkylphenylether series; solubilizing agent such as sodium cumene sulfonate and the like; acid series high molecule of such as polyacrylic acid and metallic salt thereof; corrosion inhibitor; preservative agent; anti-oxidator; disperser; anti-foam agent; and the like. Further, water into which the above materials are dissolved may include: pure water; ion exchanging water; distilled water; tap water; and the like; and moreover, may include various bleaching agents such as hypochlorous salt; hydrogen peroxide; acetyle hydroperoxide; sodium percarbonate; thiourea dioxide; and the like.

For example, in an operation at a time when a cleaning liquid containing 1-10 mass % of sodium hydroxide or potassium hydroxide is heated by a heater, not shown, disposed at an outlet of the balance tank 6 at a temperature of 50-150° C. so as to supply the cleaning liquid to the upstream side circulation path and circulate therein for 5-120 minutes. According to such operation, the interior of the upstream side pipe line section 7*a* can be appropriately cleaned, and at the same time, the sterilization in the upstream side pipe line section 7*a* can be also performed to thereby also perform the SIP treatment.

In a case where the sodium hydroxide or potassium hydroxide added to an alkaline cleaning liquid has a concentration of less than 0.2 mass %, cleaning ability to material or like of the drink adhering onto the inner surface of the pipe section is deteriorated, and on the other hand, in a case where such concentration is more than 5 mass %, the cleaning ability or sterilizing ability reaches the predetermined level, which results in unnecessary cost increasing.

Moreover, in a case where a cleaning liquid containing sodium hypochlorite having chlorite concentration of 100-3,000 ppm is used as alkaline cleaning liquid, sterilizing performance can be increased in comparison with the case of using the sodium hydroxide. In a case of the chlorine concentration being less than 100 ppm, remarkable sterilizing effect is not obtainable even if the sodium hypochlorite is added, and on the other hand, in a case of more than 3,000 ppm, the sterilizing effect more than necessity is achieved, which results in unnecessary cost increasing.

Furthermore, in a case when the temperature of the alkaline cleaning liquid now circulating is less than 50° C., the cleaning performance and the sterilizing performance are both deteriorated, and on the other hand, in a case of the circulation temperature of more than 150° C., the cleaning performance and the sterilizing performance can be sufficiently enhanced, but this temperature is difficult for operating a system.

Moreover, in a case when the alkaline cleaning liquid is circulated for a time of less than 5 minutes, the cleaning performance is deteriorated, and on the other hand, in a case of more than 120 minutes, the cleaning performance and the sterilizing performance can be sufficiently enhanced, but this temperature obstructs productivity.

After the alkaline cleaning liquid is circulated inside the upstream side circulation path so as to perform the cleaning and sterilizing treatments, the rinsing treatment is performed inside the upstream side circulation path with the aseptic water. This water may be essentially water treated with sterilizing condition over than that for the sterilization of a drink to be next produced. Such aseptic water may be prepared by heating it while flowing the water from the water supply source 23 to the UHT unit 18. The upstream side pipe line section 7*a* is cleaned by the aseptic water, and during this process, the at the same time, the interior of the upstream side pipe line section 7*a* is heated by the aseptic water to a temperature suitable for the subsequent drink filling process, thereby making it possible to promptly start the drink filling working.

Figure 3:
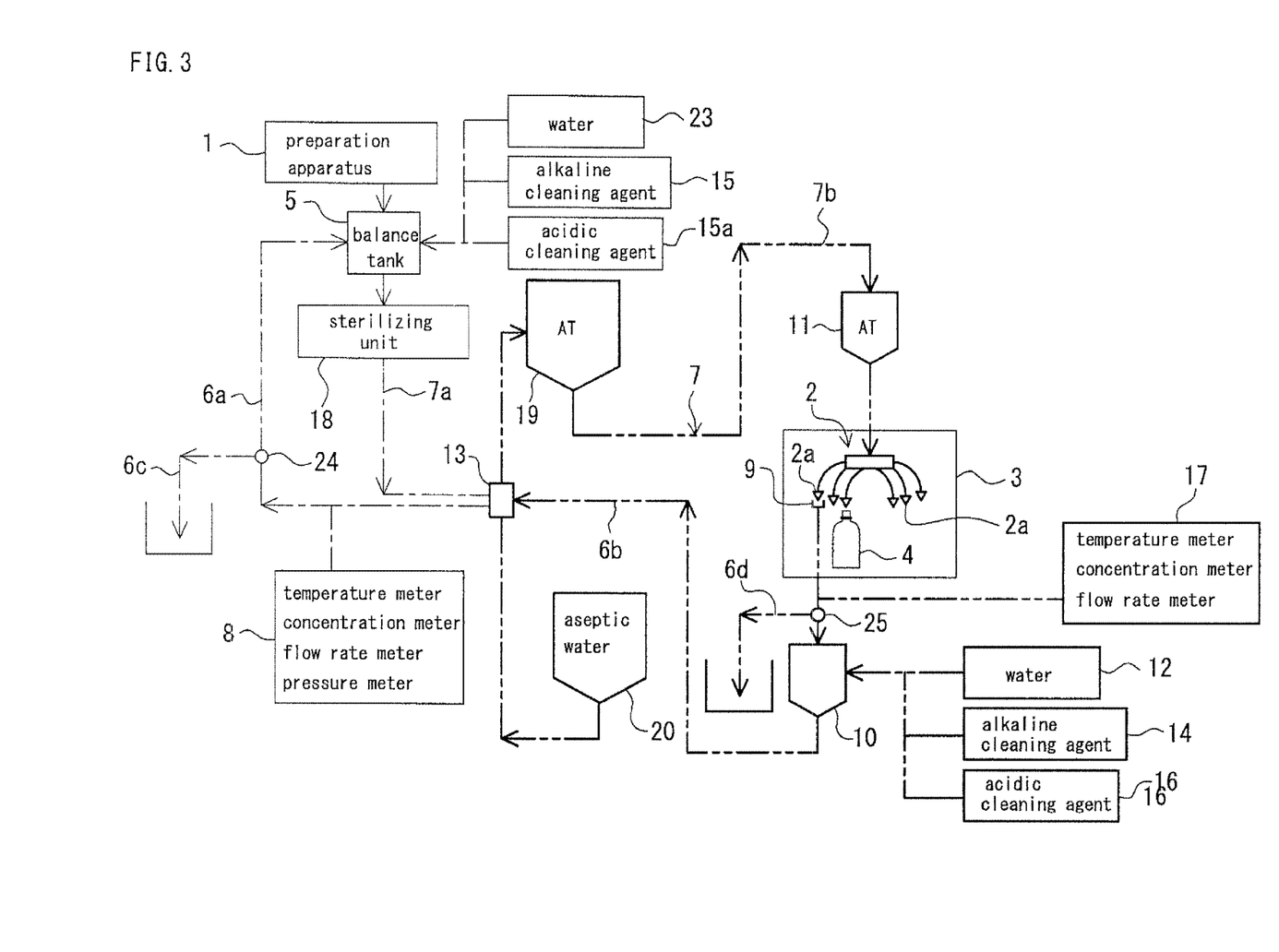
FIG. 3 is a block diagram of the aseptic drink filling system showing a state in which a CIP treatment is performed to a downstream side pipe line section of the drink filling system.

As shown in FIG. 3 with a thick line, in the drink supply pipe line 7, the downstream side return path 6*b* is provided with respect to the downstream side pipe line section 7*b* extending from the upstream side pipe line section 7*a* to the inside of the filling machine 2 through the downstream side manifold valve 13, the aseptic surge tank 19, and the head tank 11, and according to such arrangement, a downstream side circulation path is provided for the purpose of cleaning and sterilization.

The downstream side return path 6*b* is provided, at its starting end portion, with a CIP cap 9 capable of contacting to or separating from the opening of each filling nozzle 2*a* of the filling machine 2. When the CIP treatment is performed, each CIP cap 9 is applied to each opening formed to the front end portion of the nozzle 2*a* of the filling machine 2 by an actuator, so that the starting end portion of the downstream side return path 6*b* is connected to the opening of each nozzle 2*a* of the filling machine 2. Each cap 9 is connected to a manifold, not shown. The terminal end portion of the downstream side return path 6*b* extends to the manifold valve 13 through the balance tank 10.

Furthermore, in order to perform the cleaning and sterilizing treatments, an aseptic water storage tank 20 is connected to the manifold valve 13 through a supply pipe, and the water supply source 12 and the alkaline cleaning liquid supply source 14 are connected to the balance tank 10, respectively, through the supply pipes.

A drain pipe 6*d* is branched, through a valve 25, from a pipe line extending from the steam CIP cap 9 to the balance tank 10.

Further, as occasion demands, the acidic cleaning liquid supply source 16 may be connected to the balance tank 10. In a case when the cleaning is insufficiently performed only with the alkaline cleaning liquid, the acidic cleaning liquid may be circulated before the circulation of the alkaline cleaning liquid.

In addition, the water supply source 12, the alkaline cleaning liquid supply source 14 and the acidic cleaning liquid supply source 16 may be integrated with the water supply source 23, the alkaline cleaning liquid supply source 15 and the acidic cleaning liquid supply source 15*a*, respectively.

The upstream side return path 6*b* is provided, to its upstream side, with various measuring equipments 17 for measuring and detecting temperature, concentration, flow rate, pressure and the like of the alkaline cleaning liquid supplied from the alkaline cleaning liquid supply source 14.

The alkaline cleaning liquid supplied from the alkaline cleaning liquid supply source 14 is prepared with the same component as that of the alkaline cleaning liquid supplied from the alkaline cleaning liquid supply source 15 in the upstream side pipe line section 7*a*. Further, by making equal the circulation temperature and the circulating time, the cleaning and sterilizing treatments can be performed inside the downstream side pipe line section 7*b*.

Furthermore, though not shown, gas such as carbon dioxide, nitrogen, air or the like may be bubbled with the alkaline cleaning liquid so as to enhance the cleaning ability.

After the circulation of the alkaline cleaning liquid inside the downstream side circulation path and after the cleaning and sterilization treatments, it is preferred to perform the rinsing treatment to the interior of the downstream side circulation path with the aseptic water, which has been stored in the storage tank 20. Further, it is also preferred to heat the aseptic water in the storage tank 20 by a heater, not shown, provided to the outlet of the balance tank 10 and then to be supplied. At the same time of cleaning the interior of the downstream side pipe line section 7*b* with the aseptic water, the interior of the downstream side pipe line section 7b is heated by the heat transfer from the aseptic water to a temperature suitable for the subsequent drink to be filled, thereby promptly starting the filling working.

Further, the cleaning equipment described above is provided with the manifold valve 13, an actuator, not shown, various change-over valves and pumps, which are controlled by a predetermined controller, not shown, such as sequence controller or like, also not shown.

Hereunder, the cleaning method by the drink filling system mentioned above will be explained with reference to FIGS. 2 to 4.

Figure 4:
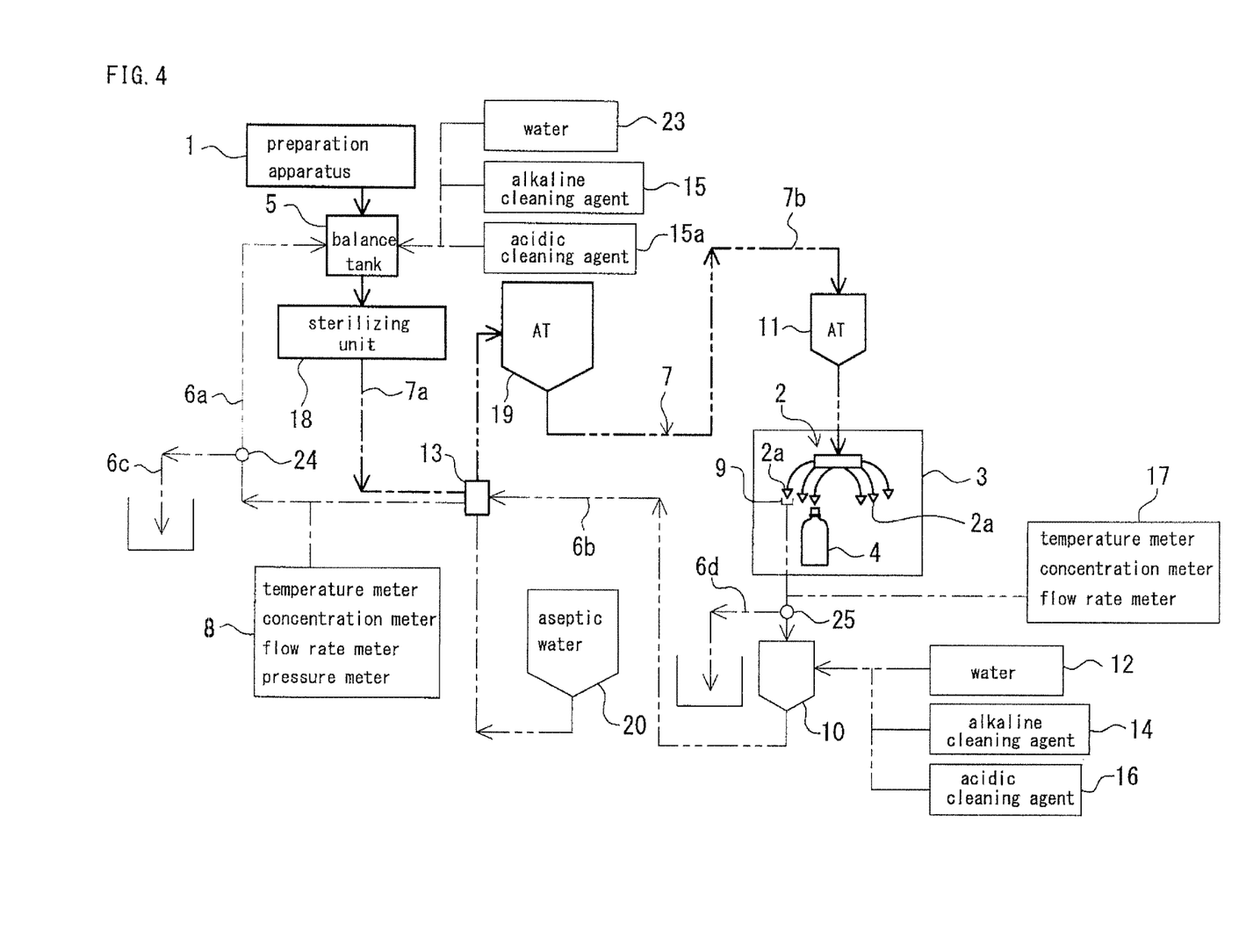
FIG. 4 is a block diagram of the aseptic drink filling system showing a state in which drink bottled products are manufactured.

(1) When an operation button provided on a sequence controller, not shown, is operated, cleaning operations of the upstream side pipe line section 7a and the downstream side pipe line section 7b of the drink supply pipe line 7 are performed with predetermined procedures (see FIGS. 3 and 4). The cleaning operations of the upstream side pipe line section 7a and the downstream side pipe line section 7b may be performed in series or in parallel to each other.

(2) Water is supplied form the water supply sources 23 and 12 respectively into the upstream side circulation path and the downstream side circulation path, and according to the circulation of such water, the interiors of the upstream side pipe line section 7a and the downstream side pipe line section 7b including the filing nozzles 2a of the filling machine 2 can be cleaned respectively in order.

(3) Next, the alkaline cleaning liquid is supplied from the alkaline cleaning liquid supply sources 15 and 14 respectively to the upstream side circulation path and the downstream side circulation path, and according to the circulation of such alkaline cleaning liquid, the interiors of the upstream side pipe line section 7a and the downstream side pipe line section 7b including the filing nozzles 2a of the filling machine 2 can be cleaned respectively in order.

The alkaline cleaning liquids circulating the respective circulation paths for cleaning the interiors of the upstream side pipe line section 7a and the downstream side pipe line section 7b are discharged outside from the drain pipes 6c and 6d, respectively, by switching the valves 24 and 25 in order after the passing of the predetermined cleaning time.

In a case where a liquid containing sodium hydroxide or potassium hydroxide of 0.1-10 mass % is used as the alkaline cleaning liquid, the alkaline cleaning liquid is heated by a heater, not shown, located to the outlet of the balance tank 5 and then supplied to the upstream side circulation path and the downstream side circulation path, respectively. By performing such circulation for 5-120 minutes, the interiors of the upstream side pipe line section 7a and the downstream side pipe line section 7b are appropriately cleaned, and at the same time, the interiors of the upstream side pipe line section 7a and the downstream side pipe line section 7b are sterilized. Accordingly, the SIP treatment can be performed without independently performing the SIP treatment as in the conventional technology.

Further, it may be allowable to use a cleaning liquid containing sodium hypochlorite having chlorite concentration of 100-3,000 ppm as alkaline cleaning liquid.

In a case when such cleaning liquid is used, it is possible to supply the cleaning liquid to the upstream side circulation path and the downstream side circulation path after heating the cleaning liquid to a temperature of 50-150° C., to thereby appropriately perform the cleaning treatment in the upstream side pipe line section 7a and the downstream side pipe line section 7b by circulating the cleaning liquid for 5-120 minutes as well as to sterilize the interiors of these pipe line sections, thereby eliminating the SIP treatment which has been required in a conventional technology.

Furthermore, as occasion demands, before the cleaning by the alkaline cleaning liquid, an acidic cleaning liquid may be supplied to the upstream side circulation path and the downstream side circulation path from the acidic cleaning liquid supply sources 15a and 16, respectively, to thereby perform the cleaning operation by the acidic cleaning liquid.

(4) After the completion of the cleaning treatment mentioned above, the rinsing treatment is performed to the interiors of the upstream side circulation path and the downstream side circulation path by circulating water or aseptic water.

The aseptic water used for rinsing the inside of the upstream side circulation path is prepared while passing the water from the water supply source 23 through the UHT unit 18. That is, it is possible to circulate the cleaning liquid while preparing the aseptic water.

The aseptic water used for rinsing the inside of the downstream side circulation path is the aseptic water preliminarily stored in the storage tank 20.

Further, when the rinsing treatment for the upstream side circulation path has been completed by the UHT unit 18, the aseptic water may be fed into the downstream side circulation path from the UHT unit 18 to thereby rinse a pipe line section disposed downstream side of the aseptic surge tank 19. The aseptic water in the storage tank 20 is the water sterilized by the heat sterilization or filtration sterilization. By such aseptic water, soot inside the downstream side pipe line section 7b is removed, and at the same time, the interior of the downstream side pipe line section 7b is cooled by heat transfer from the aseptic water to a temperature suitable for the subsequent drink filling operation. After the completion of the rinsing treatment by the cleaning agent, aseptic air for pressurization is introduced into each of the aseptic surge tanks 19 and 11 and water remaining in these aseptic surge tanks 19, 11 and the respective pipe line sections can be discharged. According to such operation, when a drink as a product liquid is delivered through the UHT unit 18, the drink is not diluted, and hence, the filling working can be smoothly started.

(5) After the completion of the cleaning treatment mentioned above, the communication between the upstream side return path 6a and the downstream side return path 6b is shut off by closing a valve, not shown, and the cap 9 is taken off from each filling nozzle 2a by operation of an actuator, not shown.

(6) When the filling working starts, the drink prepared by the preparation apparatus 1 is delivered to the filling machine 2 through the cleaned drink supply pipe line 7, and then fills the bottle 4, as a container, from the filling nozzle 2a of the filling machine 2.

It is to be noted that although the present invention is constructed as explained hereinbefore, the present invention is not limited to the described embodiment, and many changes or modifications may be made within the scope of the present invention. For example, both the balance tanks 10 and 5 may be coupled or integrated with each other to thereby form the UHT unit 18, the ACT 19, 11 and the filling machine 2 as an integrated pipe line system for performing the cleaning treatment and the sterilizing treatment at the same time. Moreover, as a container, a paper container may be used in place of bottle. An ultraviolet sterilization unit, a high pressure sterilization unit, a filtration sterilization unit or the like sterilization means may be adopted in place of the heat sterilization unit (UHT).

EXAMPLE 1

In a drink filling system for 600 bpm (bottle per minute) in which the sterilized drink fills a PET bottle, that has been sterilized in an aseptic atmosphere, having 500 mL volume, and the PET bottle is sealed with a cap, tea mixed with milk and sugar filled the PET bottle for 20 hours, and thereafter, alkaline cleaning liquid of 4 mass % sodium hydrate was prepared using the balance tank 5 shown with the thick line in FIG. 2, and then, the drink was circulated in the path line route shown with the thick line for 30 minutes at a temperature of 85° C.

Further, the alkaline cleaning liquid of 4 mass % sodium hydrate was prepared using the balance tank 10 shown with the thick line in FIG. 3, and then, the drink was circulated in the path line route shown with the thick line for 30 minutes at a temperature of 85° C.

Thereafter, the aseptic water of normal temperature was fed from the aseptic water tank 20 to the balance tank 5 and then delivered along the line shown with the thick line in FIG. 4 so as to perform the rinsing treatment. After the rinsing treatment, green tea filled the PET bottles 4 for continuous 15 hours. In such filling operation, no rotten was found out to every PET bottle as drink filled product bottle.

EXAMPLE 2

In a drink filling system for 600 bpm (bottle per minute) which was sealed by a sterilized cap and a sterilized drink then filled a PET bottle, that has been sterilized in an aseptic atmosphere, having 500 mL volume, green tea filled for 20 hours, and thereafter, alkaline cleaning liquid of 2 mass % sodium hydrate was prepared using balance tank 5 shown with the thick line in FIG. 2, and then, the drink was circulated in the path line route shown with the thick line for 20 minutes at a temperature of 85° C.

Further, the alkaline cleaning liquid of 2 mass % sodium hydrate was prepared using balance tank 10 shown with the thick line in FIG. 3, and then, the drink was circulated in the path line route shown with the thick line for 20 minutes at a temperature of 85° C. Thereafter, the aseptic water of normal temperature was fed from the aseptic water tank 20 to the balance tank 5 and then delivered along the line shown with the thick line in FIG. 4 so as to perform the rinsing treatment. After the rinsing treatment, barley tea filled the PET bottles 4 for continuous 15 hours. In such drink filling operation, no rotten was found out to every PET bottle as drink filled product bottle.

EXAMPLE 3

In a drink filling system for 600 bpm (bottle per minute) which was sealed by a sterilized cap and a sterilized drink filled a PET bottle, that has been sterilized in an aseptic atmosphere, having 500 mL volume, barley tea filled for 20 hours, and thereafter, the alkaline cleaning liquid including 0.5 mass % potassium hydrate and 600 ppm chlorine concentration sodium hypochlorite was prepared using balance tank 5 shown with the thick line in FIG. 2, and then, the drink was circulated in the path line route shown with the thick line for 20 minutes at a temperature of 75° C. Furthermore, the alkaline cleaning liquid including 0.5 mass % potassium hydrate and 600 ppm chlorine concentration sodium hypochlorite was prepared using balance tank 10 shown in FIG. 3, and then, the drink was circulated in the path line route shown with the thick line for 20 minutes at a temperature of 75° C. Thereafter, the aseptic water of normal temperature was fed from the aseptic water tank 20 to the balance tank 5 and then delivered along the line shown with thick line in FIG. 4 so as to perform the rinsing treatment. After the rinsing treatment, tea mixed with milk filled the PET bottles 4 for continuous 15 hours. In such filling operation, no rotten was found out to every PET bottle as drink filled product bottle.

Exemplary Embodiment 2

Figure 5:
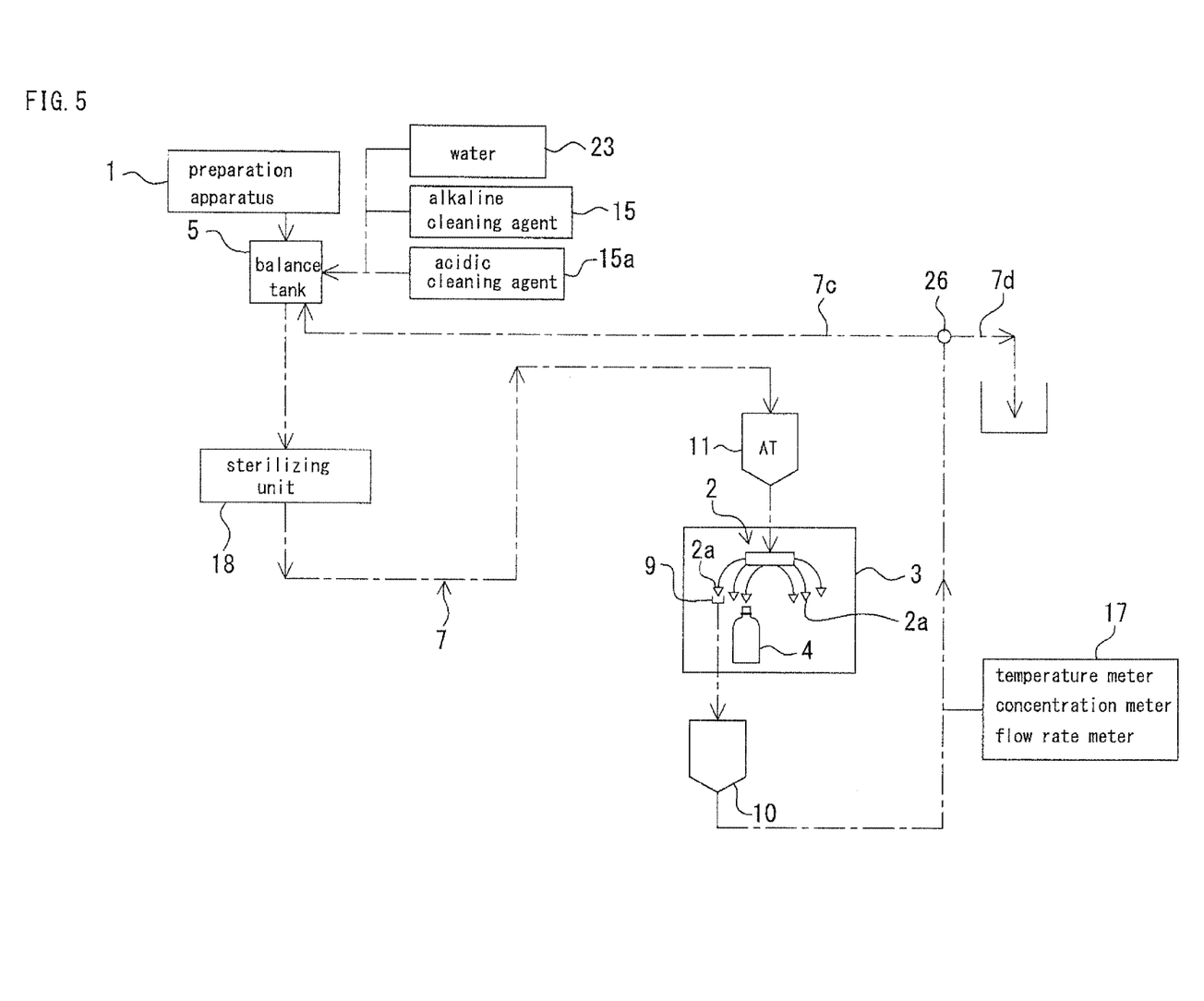
FIG. 5 is a block diagram of an aseptic drink filling system for carrying out a drink filling method according to another embodiment of the present invention.

As shown in FIG. 5, the drink supply pipe line 7 of the drink filling system of the present embodiment is provided, between a pipe line section extending from the preparation apparatus 1 to the filling machine 2, with the balance tank 5, the sterilizing unit (UHT) 18, and the head tank 11 in this order from the upstream side to the downstream side in the drink delivering direction, and the pipe line section enters the filling machine 2 from the head tank 11.

Figure 6:
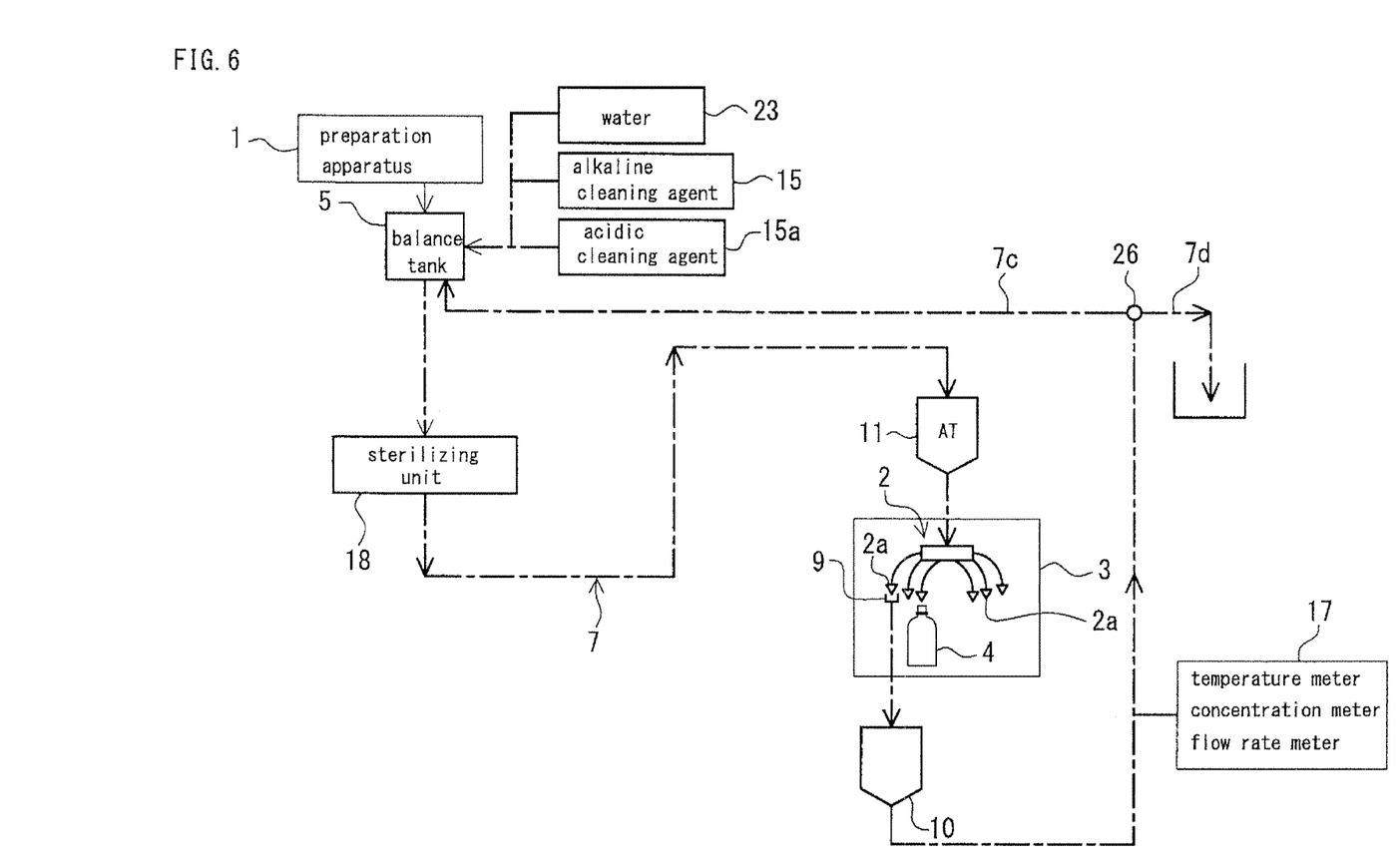
FIG. 6 is a block diagram of the aseptic drink filling system showing a state in which a CIP treatment is performed to a drink supply pile line of the drink filling system.

As shown with the thick line in FIG. 6, the water supply source 23 and the alkaline cleaning liquid supply source 15 are connected respectively to the balance tank 5 through the supply pipes for performing the cleaning and sterilizing treatments. Further, as occasion demands, the acidic cleaning liquid supply source 15a may be also connected to the balance tank 5.

The alkaline cleaning liquid delivered from the alkaline cleaning liquid supply source 15 may use one having substantially the same composition of that of the first embodiment 1.

As shown in FIG. 6 with the thick line, a return path 7c is disposed substantially in parallel with the drink supply pipe line 7 mentioned above. The return path 7c is provided with caps 9 each facing an opening of each of the filling nozzles 2a at the starting end side of the return path 7c to be contactable to or separable from the opening. When the CIP treatment is performed, the cap 9 is applied to the front opening of the filling nozzle 2a of the filling machine 2 by an actuator, not shown, and thus, the starting end portion of the return path 7c is connected to the opening of the filling nozzle 2a. The return path 7c extends toward a manifold, not shown, from each cap 9 and then extends to the balance tank 5 through the balance tank 10.

The circulation path for carrying out the cleaning and sterilizing treatments is provided within the drink supply pipe line 7 by connecting the return path 7c to the drink supply pipe line 7.

A drain pipe 7d is connected to the return path 7c, and the drain pipe 7d is equipped with various measuring devices 17 for measuring and detecting temperature, concentration, flow rate, pressure and so on of the alkaline cleaning liquid flowing the circulation path passing through the balance tank 5 and the sterilizing unit 18 after being supplied from the alkaline cleaning liquid supply source 15.

After cleaning and sterilizing the inside of the drink supply pipe line 7 by circulating the alkaline cleaning liquid within the circulation path, the rinsing treatment with water is performed to the interior of the circulation path. The water to be used for such rinsing treatment may be prepared by supplying the water from the water supply source 23 and heating the water during the passing inside the sterilizing unit 18 such as UHT. Furthermore, it may be desired for such water to be sterilized with sterilizing effect more than that allowable for a drink that is preliminarily scheduled to be supplied inside the drink supply pipe line 7 in the subsequent drink filling operation.

At the same time when this water is rinsed and then cleaned in the drink supply pipe line 7, the interior of the drink supply pipe line 7 is cooled by the heat transferred to the water to a temperature suitable for the subsequent drink filling operation, thereby smoothly and speedily starting the filling working.

Figure 7:
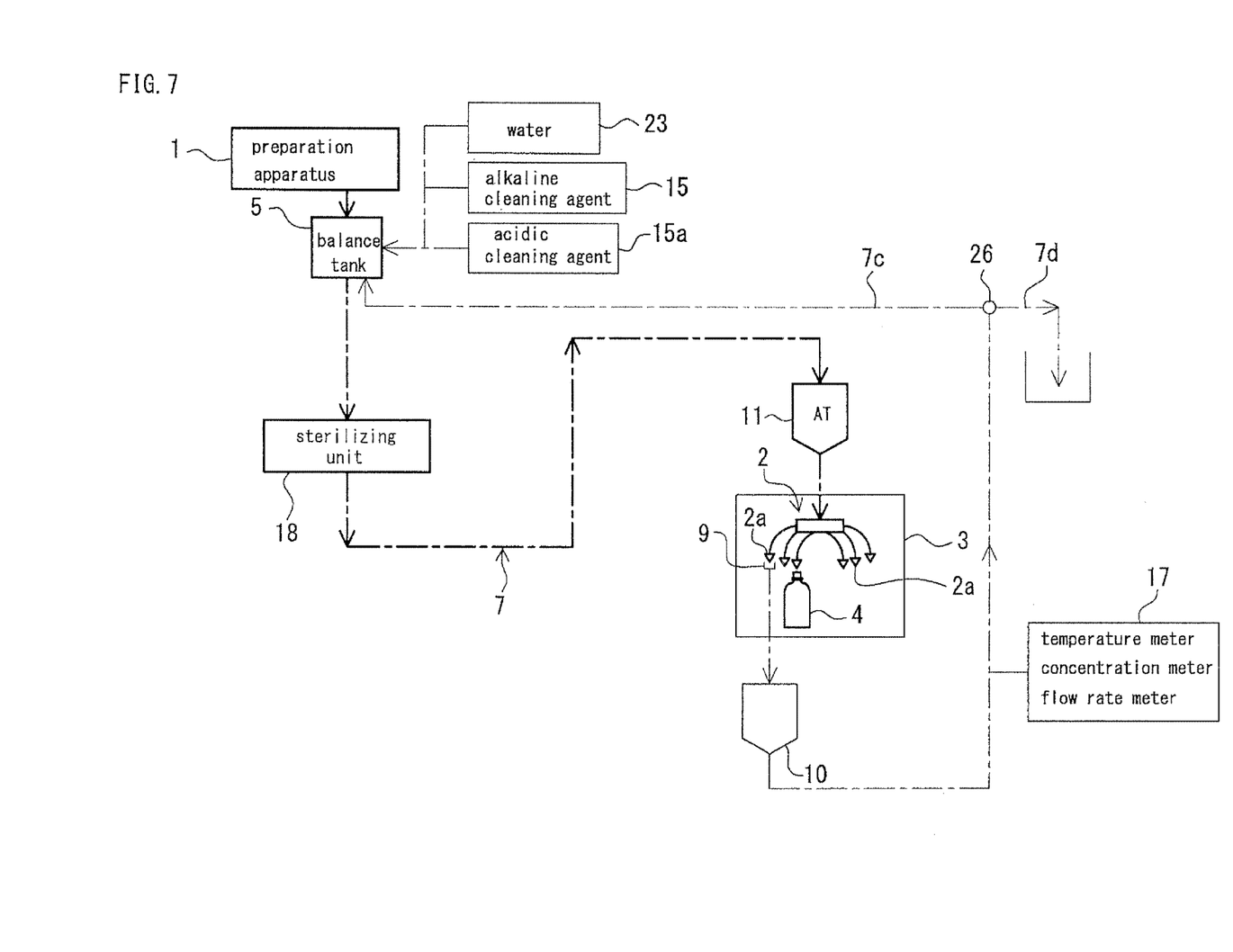
FIG. 7 is a block diagram of the aseptic drink filling system showing a state in which drink bottled products are manufactured.

The drink filling system cleaning method will be described hereunder with reference to FIGS. 6 and 7.

(1) When an operation button provided on a panel of a sequence controller, not shown, is operated, the cleaning operation of the drink supplying pipe line 7 is performed in accordance with a predetermined procedure.

(2) The water is supplied form the respective water supply sources 23 into the drink supply pipe line 7 to thereby clean the interior of the drink supply pipe line 7. The water supplied in the drink supply pipe line 7 circulates inside the circulation path for a predetermined time, and thereafter, discharged outside from the drain pipe 6d as waste water.

(3) Next, the alkaline cleaning liquid is supplied from each of the respective alkaline cleaning liquid supply sources 15 and circulates inside the circulation path for a predetermined time. According to the circulation of the supplied the alkaline cleaning liquid, the interior of the drink supply pipe line 7 extending from the balance tank 5 to the filling nozzle 2a of the filling machine 2 can be cleaned and sterilized simultaneously.

The alkaline cleaning liquid supplied into the drink supply pipe line 7 circulates inside the circulation path for the predetermined time, and thereafter, is discharged outside from the drain pipe 7d as waste liquid.

In a case where a liquid containing sodium hydroxide or potassium hydroxide of 0.1-10 mass % is used as the alkaline cleaning liquid, the alkaline cleaning liquid is heated by a heater, not shown, located to the outlet portion of the balance tank 5 to a temperature of 50-150° C. and then supplied to the circulation path. By performing such circulation for 5-120 minutes, the interior of the drink supply pipe line 7 can be appropriately cleaned, and simultaneously, the interior thereof can be also sterilized. Accordingly, the SIP treatment can be simultaneously performed without independently performing such SIP treatment as performed in the conventional technology.

Further, it may be allowable to use a cleaning liquid containing sodium hypochlorite having chlorite concentration of 100-3,000 ppm as alkaline cleaning liquid.

In a case when such cleaning liquid is used, it is possible to supply the cleaning liquid to the drink supply pipe line 7 after heating to a temperature of 50-150° C. and to appropriately perform the cleaning treatment to the interior of the drink supply pipe line 7 for 5-120 minutes as well as to sterilize the interior of such drink supply pipe line, thereby eliminating the SIP treatment which has been performed in a conventional technology.

Furthermore, as occasion demands, before the cleaning by the alkaline cleaning liquid, an acidic cleaning liquid may be supplied to the circulation path from the acidic cleaning liquid supply source 15a to thereby perform the cleaning treatment to the inside of the drink supply pipe line 7 by the acidic cleaning liquid.

(4) After the completion of the cleaning treatment mentioned above, the rinsing treatment is performed to the interior of the circulation path including the drink supply pipe line 7 by the water.

The water used for rinsing the inside of the drink supply pipe line 7 is prepared while passing the water from the water supply source 23 as the UHT unit 18, for example. Further, it may be desired that such rinsing water is treated with sterilizing effect more than that allowable for a drink to be supplied in the interior of the drink supply pipe line at the next drink filling procedure.

(5) After the completion of the cleaning treatment mentioned above, the valve 26 is closed, and then, the cap 9 is removed from the opening of each filling nozzle 2a by the actuator, not shown.

(6) When the next drink filling working starts, the drink newly prepared by the preparation apparatus 1 is delivered to the filling machine 2 through the cleaned drink supply pipe line 7, and then fills the bottle 4, as a container, from the filling nozzle 2a of the filling machine 2.

It is to be noted that the present invention is not limited to the drink filling method and the drink filling system in the aseptic filling line, and is applicable to all manufacturing equipments or facilities in which product liquid line should be sterilized before manufacturing of drink packages or containers such as hot pack line, child drink line and the like.

REFERENCE NUMERAL

2—filling machine
6a—upstream side return path
6b—downstream side return path
7—drink supplying pipe line
7a—upstream side pipe line section
7b—downstream side pipe line section
18—sterilizing unit

The invention claimed is:

1. A drink filling method, comprising:
sterilizing a drink supply pipe line for supplying a drink from a heat-sterilizing unit into a filling machine,
filling a sterilized container with the drink supplied from the drink supply pipe line, and,
sealing the container,
wherein an upstream side circulation path is formed by forming an upstream side return path to an upstream side pipe line section passing through a first balance tank and the sterilizing unit of the drink supply pipe line, the first balance tank being connected with a first water supply source and a first alkali cleaning liquid supply source,
wherein a downstream side circulation path is formed by forming a downstream side return path, being formed of a nozzle of a filling machine to a manifold valve via a second balance tank connected with a second water supply source and a second alkali cleaning liquid supply source, to a downstream side pipe line section of the drink supply pipe line extending from a downstream side portion of the upstream side pipe line section to the filling machine,
circulating an alkali cleaning liquid within the upstream side circulation path and the downstream side circulation path for a predetermined time to thereby clean and sterilize an interior of the drink supplying pipe line, the circulating the alkali cleaning liquid within the upstream side circulation path and the circulating the alkali cleaning liquid within the downstream side circulation path being performed in parallel with each other, and
applying a rinsing treatment to an interior of the upstream side circulation path and the downstream side circulation path with an aseptic water sterilized by heat sterilization under a heat sterilization condition greater than a heat sterilization condition of a drink to be subsequently supplied,
wherein the aseptic water circulating the upstream side circulation path is sterilized by the heat-sterilizing unit, and wherein the aseptic water circulating the downstream side circulation path is sterilized by a heater provided to an outlet of the second balance tank.

2. The drink filling method according to claim 1, wherein the water used for the rinsing treatment is set to have a same temperature as that of the drink to be filled.

3. The drink filling method according to claim 1, wherein the alkaline cleaning liquid is a cleaning liquid including at least 0.1-10 mass % of sodium hydroxide or potassium hydroxide.

4. The drink filling method according to claim 1, wherein the alkaline cleaning liquid is a cleaning liquid at least including sodium hypochlorite having chlorine concentration of 100-3,000 ppm.

5. The drink filling method according to claim 1, wherein the alkaline cleaning liquid is supplied by being heated to a temperature of 50-150° C.

6. The drink filling method according to claim 1, wherein the predetermined time for alkaline cleaning liquid to be circulated is 5-120 minutes.

7. The drink filling method according to claim 1, wherein the alkaline cleaning liquid is supplied with addition of a bleaching agent.

\* \* \* \* \*